(12) United States Patent
Wang et al.

(10) Patent No.: US 11,008,379 B1
(45) Date of Patent: May 18, 2021

(54) PREPARATION OF PURIFIED COLLAGEN SOLUTION FROM PORCINE SKIN

(71) Applicants: Qi Wang, Fullerton, CA (US); Dae Kyu Chang, Fullerton, CA (US)

(72) Inventors: Qi Wang, Fullerton, CA (US); Dae Kyu Chang, Fullerton, CA (US)

(73) Assignee: Sigmagraft, Inc., Fullerton, CA (US)

( * ) Notice: Subject to any disclaimer, the term of this patent is extended or adjusted under 35 U.S.C. 154(b) by 0 days.

(21) Appl. No.: 16/356,094

(22) Filed: Mar. 18, 2019

(51) Int. Cl.
| | |
|---|---|
| *C07K 14/78* | (2006.01) |
| *C07K 1/14* | (2006.01) |
| *C07K 1/34* | (2006.01) |
| *B01D 29/56* | (2006.01) |
| *B01D 37/00* | (2006.01) |

(52) U.S. Cl.
CPC .............. *C07K 14/78* (2013.01); *B01D 29/56* (2013.01); *B01D 37/00* (2013.01); *C07K 1/145* (2013.01); *C07K 1/34* (2013.01)

(58) Field of Classification Search
CPC .......... C07K 1/34; C07K 1/145; C07K 14/78; B01D 29/56; B01D 37/00
USPC ......................................................... 435/325
See application file for complete search history.

(56) References Cited

U.S. PATENT DOCUMENTS

2008/0188642 A1* 8/2008 Ying ..................... C08H 1/00
530/356
2017/0334969 A1* 11/2017 Chang ................. A61L 27/3687

* cited by examiner

*Primary Examiner* — Jennifer M. H. Tichy
(74) *Attorney, Agent, or Firm* — Plager Schack LLP; Mark H. Plager; Kara Verryt

(57) ABSTRACT

A method of preparing a purified collagen solution from porcine skin may include receiving and inspecting the porcine skin; treating the porcine skin with a sodium hydroxide treatment, resulting in a sodium hydroxide processed skin; treating the sodium hydroxide processed skin with an ethanol treatment, resulting in ethanol treated processed skin; producing liquid collagen from the ethanol treated processed skin; clarifying the liquid collagen; and concentrating the clarified liquid collagen.

10 Claims, 6 Drawing Sheets

PREPARATION OF PURIFIED COLLAGEN SOLUTION FROM PORCINE SKIN

BACKGROUND

The embodiments herein relate generally to the preparation of collagen, and more particularly, to a method for extracting and purifying a collagen solution from porcine skin.

Collagen is the most abundant protein in mammals and makes up around 30% of total protein weight in the body. It is the main component of various connective tissue, such as tendons, ligaments, and skin. The applications of collagen and its related products are increasing rapidly, especially in cosmetics and biomedical fields.

There are many types of collagen, but type one collagen is the main type of collagen in many tissues, including porcine skin. The structural unit of type one collagen is tropocollagen, which is composed of three polypeptide chains, two $\alpha_1$ chains and one $\alpha_2$ chain. These a chains form a triple helical structure through hydrogen bonds. When running a sodium dodecyl sulfate polyacrylamide gel electrophoresis (SDS-PAGE) to confirm collagen content, there are usually bands of $\beta$ and $\gamma$ chains, which are dimers and trimers of a chains, respectively.

Collagen has a high content of hydroxyproline that is not usually found in other proteins, which is used to characterize collagen specifically. For example, after collagen is decomposed by acid or enzymes into peptides, a hydroxyproline assay can be conducted to measure the concentration of hydroxyproline, and thus calculate the concentration of collagen.

Numerous methods have been developed to extract and purify collagen from various animal tissues, such as tendon, cartilage, skin, and bone. For example, U.S. Pat. No. 5,064,941 to Davison teaches extracting collagen from animal collagen containing tissue using organic diamines or an amino-alcohol salt solution. However, the extracted collagen has some other protein impurities, and the chemicals used are considered toxic. U.S. Pat. No. 6,271,350 to Shimizu teaches extracting collagen from raw fish skin by first admixing a salt with raw fish, followed with heating the skin to 80° C. to extract collagen. However, the heating step may denature and transfer most of the collagen into gelatin, which is not an ideal way to extract collagen molecules in its natural status. U.S. Pat. No. 6,995,242 to Nnanna discloses extracting and fractionating collagen-rich proteinaceous materials from poultry skin tissue, wherein the poultry skin tissues are heated between 60° C. and 100° C. and then centrifuged to separate solid phase and liquid phase. However, the collagen achieved from this method contains a lot of impurities and denatured collagen.

Collagen is susceptible to decomposition by collagenase while it is not susceptible to other proteolytic enzymes, such as trypsin, pepsin, elastase, etc. This property allows for the separation of collagen from various tissues, which has been reported by several previous inventions. For example, U.S. Pat. No. 7,109,300 to Losso teaches treating calcified tissue with an aqueous solution of acid and pepsin to extract collagen from the tissue into an aqueous solution. U.S. Pat. No. 7,396,912 to Hsiao discloses solubilizing fermented collagen-containing tissue with pepsin provided at about 0.2% w/v to about 5% w/v at low temperatures and in an acetic acid solution (pH=3). U.S. Pat. No. 7,781,158 to Yu discloses adding pepsin dissolved in 0.1N HCl to acid-treated bone tissue powder in a ratio of tissue:pepsin from 10:1 to 50:1 to extract collagen from the bone tissue. However, this enzymatic extraction method has some disadvantages, including incomplete hydrolysis, long reaction time, and strict reaction conditions.

Thus, existing porcine collagen extraction methods often involve numerous steps, and the extracted collagen is not purified and, thus, contains higher amounts of impurities.

Therefore, what is needed is an efficient method for extracting collagen from porcine skin, wherein the extracted collagen is highly purified.

SUMMARY

Some embodiments of the present disclosure include a method of preparing a purified collagen solution from porcine skin. The method may include receiving and inspecting the porcine skin; treating the porcine skin with a sodium hydroxide treatment, resulting in a sodium hydroxide processed skin; treating the sodium hydroxide processed skin with an ethanol treatment, resulting in ethanol treated processed skin; producing liquid collagen from the ethanol treated processed skin; clarifying the liquid collagen; and concentrating the clarified liquid collagen.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
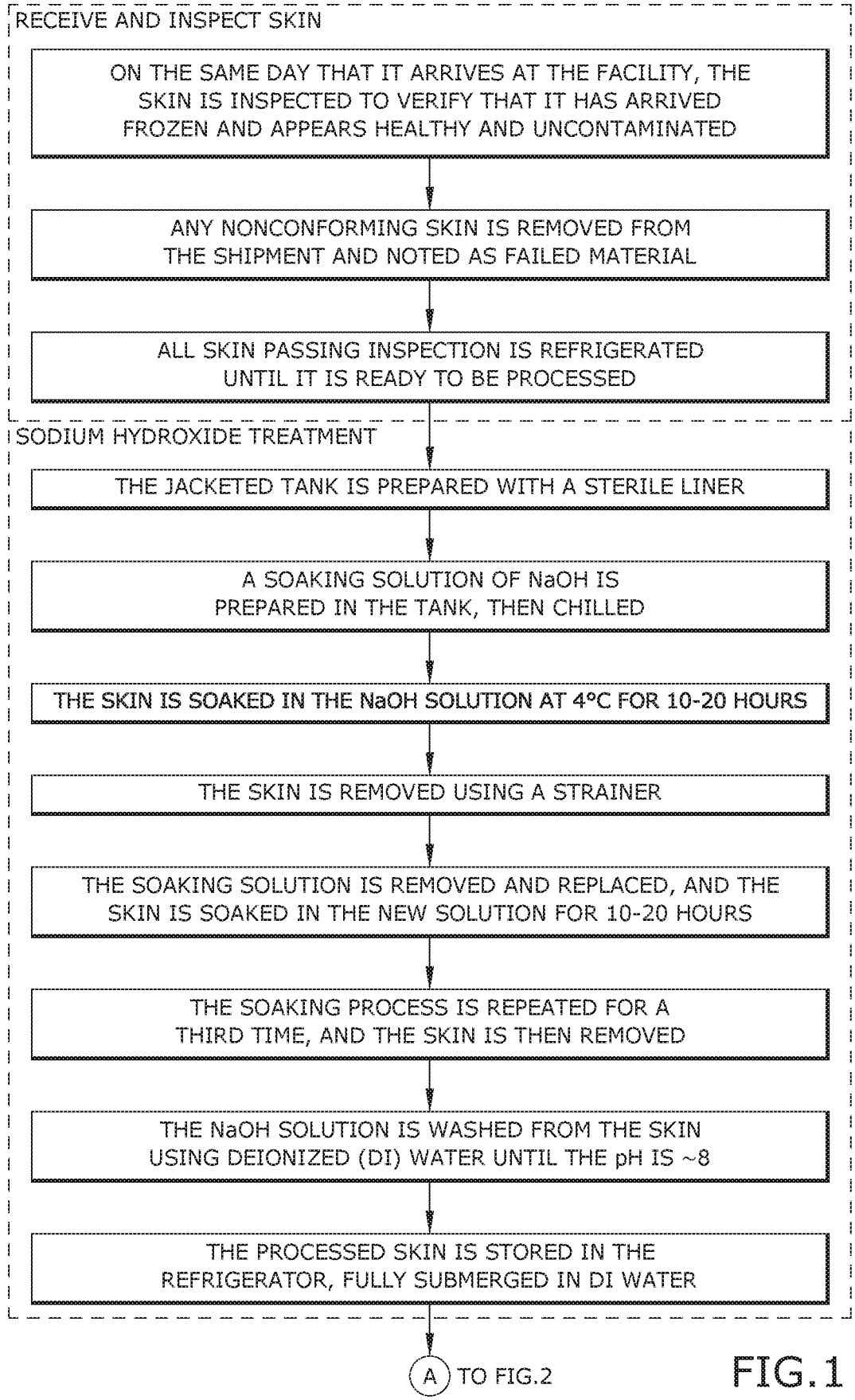
FIG. 1 is a flow chart describing one embodiment of the present disclosure.
Figure 2:
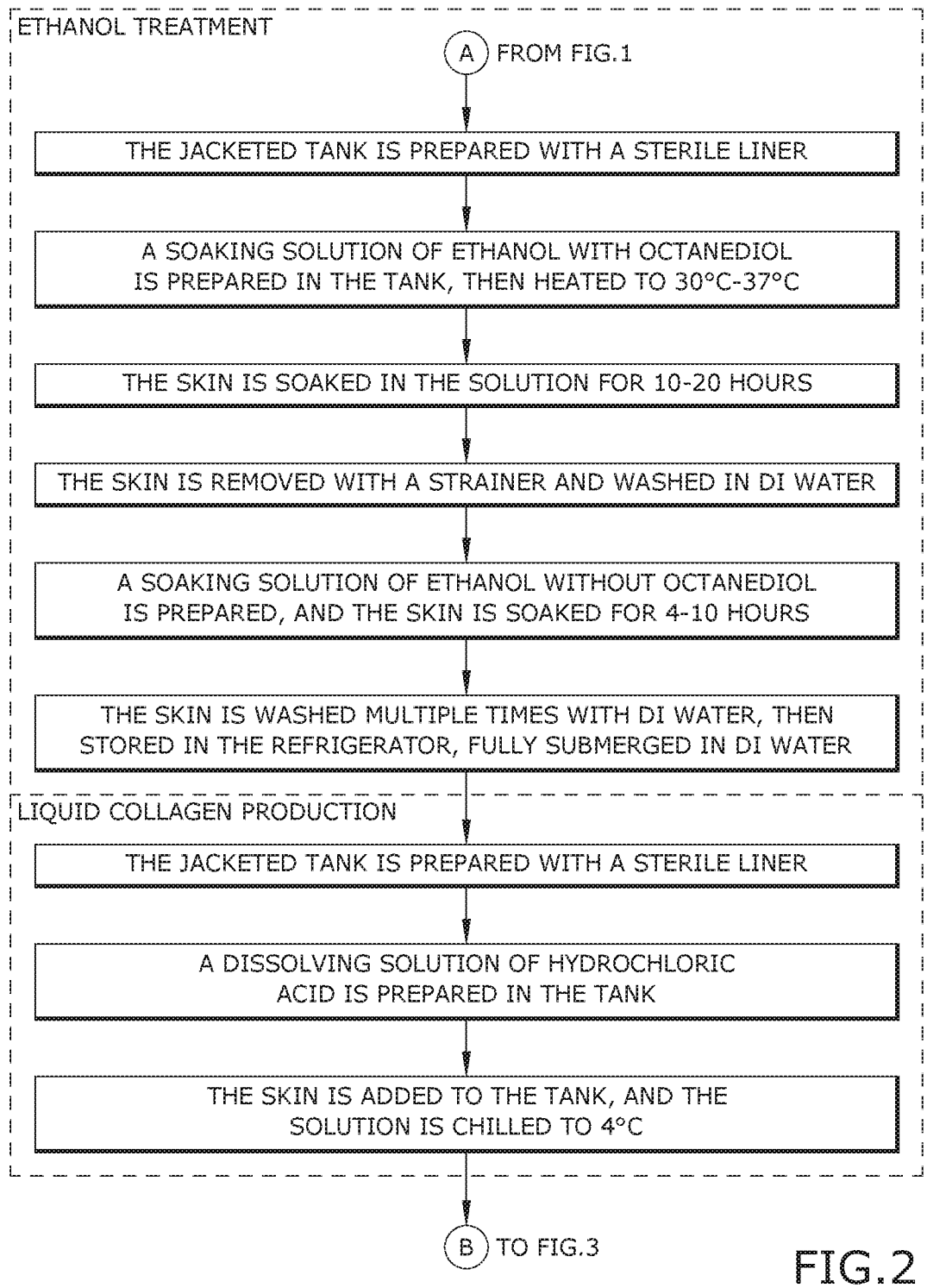
FIG. 2 is a continuation of FIG. 1.
Figure 3:
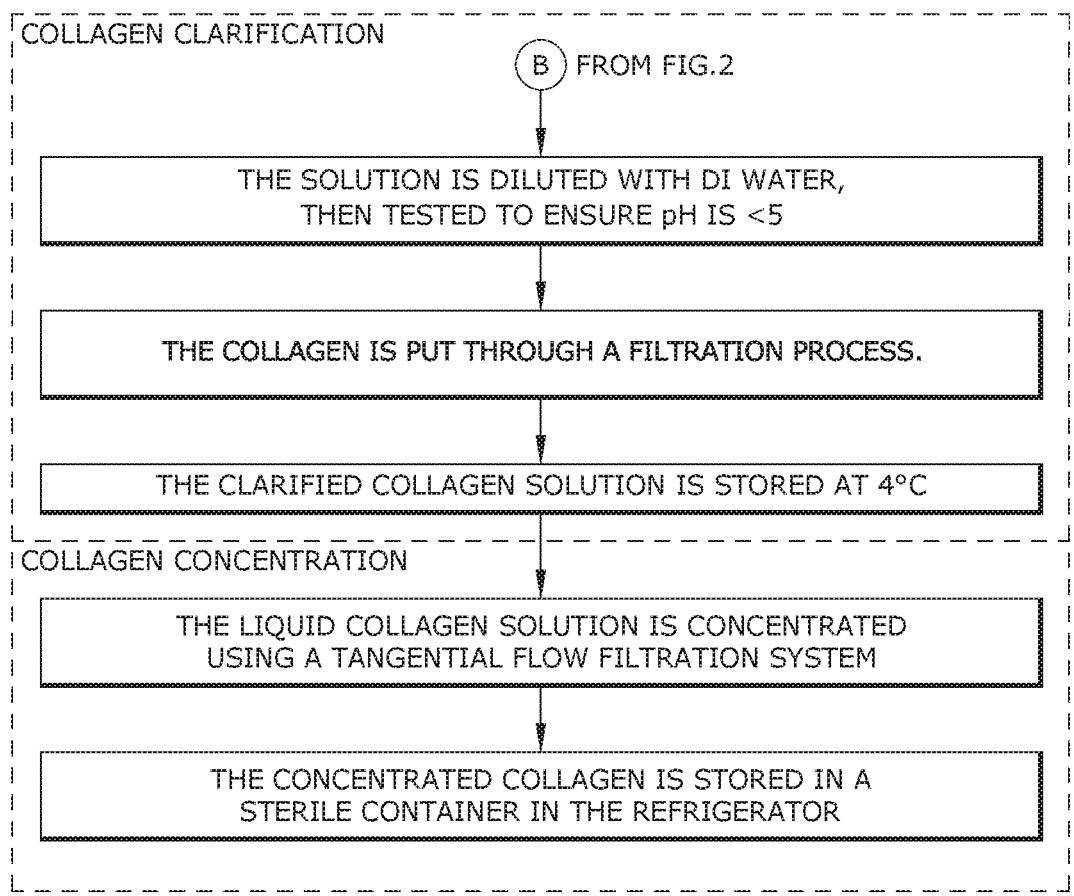
FIG. 3 is a continuation of FIG. 2.

In the following detailed description of the invention, numerous details, examples, and embodiments of the invention are described. However, it will be clear and apparent to one skilled in the art that the invention is not limited to the embodiments set forth and that the invention can be adapted for any of several applications.

The method of the present disclosure may be used to extract and purify collagen from porcine skin and may comprise the following elements. This list of possible constituent elements is intended to be exemplary only, and it is not intended that this list be used to limit the method of the present application to just these elements. Persons having ordinary skill in the art relevant to the present disclosure may understand there to be equivalent elements that may be substituted within the present disclosure without changing the essential function or operation of the method.

a. Receiving and Inspecting Skin
b. Sodium Hydroxide Treatment
c. Ethanol Treatment
d. Liquid Collagen Production e. Collagen Clarification f. Collagen Concentration The various elements of the method of the present disclosure may be related in the following exemplary fashion. It is not intended to limit the scope or nature of the relationships between the various elements and the following examples are presented as illustrative examples only.

By way of example, and referring to FIGS. 1-5, some embodiments of the present disclosure include a method of preparing a purified collagen solution from porcine skin. The process may, generally, include two steps: extracting the collagen from porcine skin and purifying a collagen solution via filtration. Extracting collagen may involve removing the connective fat tissue by mechanical means, soaking the porcine skin in a solution of sodium hydroxide and in a solution of ethanol with octanediol, and dissolving the porcine skin tissue in an acid solution. The extracting step may remove non-collagen proteins, fats, cell tissue pieces, and the like. Purifying the collagen solution may involve filtering the dissolved porcine skin collagen solution using a multistage filtration system. The purifying step may remove small fat particles, lipid aggregates, and other impurities to clarify the collagen solution. A final concentration step may be used to concentrate collagen to the desired concentration. The resulting porcine derived collagen solution may be highly purified and may be used for medical and cosmetic applications.

More specifically, the method may comprise receiving and inspecting the porcine skin; treating the porcine skin with a sodium hydroxide treatment, resulting in a sodium hydroxide processed skin; treating the sodium hydroxide processed skin with an ethanol treatment, resulting in ethanol treated processed skin; producing liquid collagen from the ethanol treated processed skin; clarifying the liquid collagen; and concentrating the clarified liquid collagen. The method may further comprise analyzing the concentrated collagen to ensure desired and proper levels of purification.

As mentioned above, the first step in the method of the present disclosure may comprise receiving and inspecting the porcine skin. Inspection may be performed on the same day the pericardia arrives. To pass inspection, the skin may arrive frozen and be visually inspected for healthy, uncontaminated tissue. If the skin is nonconforming, it may not be used in the method of the present disclosure. Examples of non-conforming skin may include inflammation, masses, lesions, or evidence of microbial contamination or disease, while conforming skin may appear free of disease.

Figure 6:
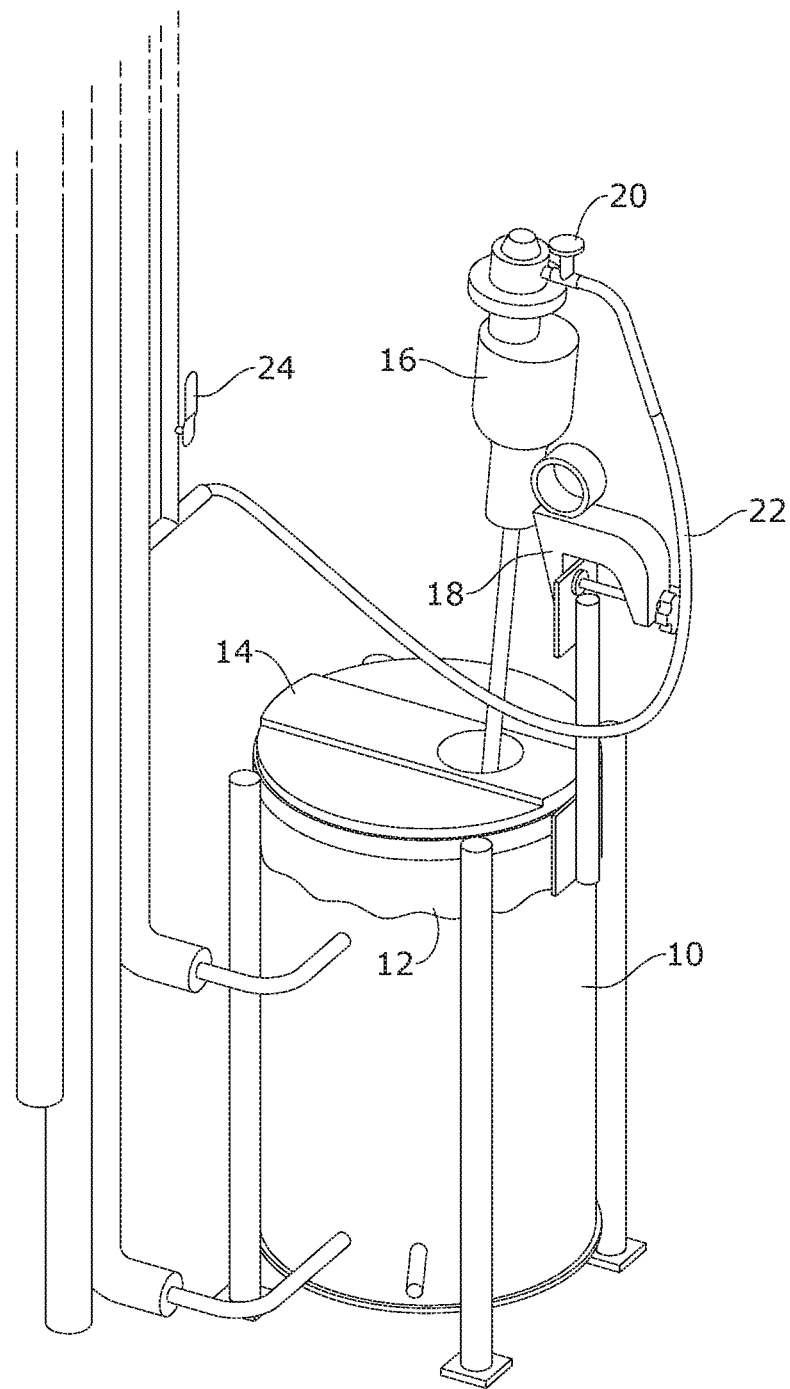
FIG. 6 is a schematic view of an exemplary tank set up used in the method of the present disclosure.

Treating with a sodium hydroxide treatment may first comprise first preparing a NaOH soaking solution with a concentration between 0.2M and 1M from a 1M stock solution, wherein the soaking solution is combined with the raw skin at a ratio of 1 g:10 mL to 1 g:40 mL NaOH to raw skin. The appropriate volume of NaOH may be added to a tank including a sterile liner, wherein the tank may be cleaned using, for example, isopropyl alcohol, prior to the addition of NaOH. A cover may be placed on the tank and the soaking solution may be chilled by setting the chiller to a temperature of, for example, about 4° C. During chilling of the soaking solution, the temperature may be monitored. Once the temperature is less than about 20° C., the raw skin may be washed with deionized water, wherein the volume of deionized water is large enough to allow for the submersion of all of the skin tissue for about 1 to about 5 minutes, and then loaded into the tank. An exemplary tank set up is shown in FIG. 6, wherein the tank set up may comprise a tank 10 with a sterile tank liner 12 sized to accommodate a volume of liquid and a tank cover 14 operatively attached to and closing off the top of tank 10. A pneumatic motor 16 may be assembled and operatively attached to the tank 10, wherein an air-line 22 connected to the tank may be turned on and an impellor attached to the pneumatic motor 16 may mix the contents of the tank 10 vigorously, wherein vigorously mixing results in the skin circulating in the tank without being shredded. A pressure regulator 20 may also be operatively attached to the motor 16. In some embodiments, the motor 16 and pressure regulator 20 assembly may be held in place by a clamp 18 operatively attached to the tank 10. The air-line 22 may attach the pressure regulator 20 to an air valve 24 attached to an air supply. While FIG. 6 shows an exemplary tank set up, other assemblies may also be suitable.

The raw skin may be allowed to soak in the soaking solution for about 18 to about 22 hours, such as for about 20 hours. Following soaking, the temperature of the soaking solution may be measured and recorded. A strainer may then be used to recover the skin from the tank, and the recovered skin may be stored at a temperature of about 2° C. to about 8° C. The above soaking procedure may be repeated for two additional soaking periods, resulting in the raw skin being soaked in a NaOH soaking solution for a total time of about 60 hours. Following the last soaking period, the sodium hydroxide treated skin may be transferred into a container containing deionized water, wherein the volume of deionized water is large enough to allow for the submersion of all of the skin tissue. The skin may be mildly agitated with, for example, a ladle, for about 1 to about 5 minutes, such as for about 2 minutes, and the solution may be discarded, leaving just the sodium hydroxide treated skin. The treated skin may be loaded back into the tank with deionized water, wherein the volume of deionized water may be about two times the amount of NaOH used. The treated skin and water may be stirred vigorously, and the treated skin may be allowed to soak for 4 hour increments or overnight. The pH of the solution may be tested and the soaking in deionized water may be repeated until the pH is about 8. Once the desired pH is achieved, the processed skin may be stored at a temperature of from about 2° C. to about 8° C. while fully submerged in deionized water.

As mentioned previously, after the skin has been treated with the sodium hydroxide treatment, it may then undergo an ethanol treatment. First, the ethanol solution may be prepared. For example, the ethanol solution may be prepared using 40% to 80% ethanol with –5-10% 1,2-octanediol (w/v) soaking solution. The same tank setup used in the sodium hydroxide treatment may be used for the ethanol treatment. The appropriate volume of ethanol solution and skin may be added to the tank. The air line may be turned on and the speed of the mixer may be adjusted such that the skin is stirred vigorously. The solution may be heated to a temperature of about 30° C. to about 37° C., such as 37° C., and the skin may be allowed to soak for about 20 hours. During soaking, the temperature of the solution may be monitored and, if the temperature rises above about 38° C., the circulator may be adjusted. Soaking at a temperature above about 40° C. may denature the collagen. After soaking, the tissue may be recovered and transferred into a container containing deionized water, wherein the volume of deionized water is large enough to fully submerge the tissue. The membranes may be mildly agitated by hand with a ladle for no less than about 2 minutes. The agitation may be repeated about 3 times in new deionized water each time After agitating the tissue, a volume of 40% to 80% ethanol (this time without the 1,2-octanediol) may be added to the tank and the skin may be soaked for about 4 hours. The volume of 40% to 80% % ethanol may be equal to the volume used during the initial soaking using ethanol and octanediol. After soaking, the tissue may be transferred into a container containing enough deionized water to fully submerge the tissue. The membranes may be mildly agitated with a ladle for no less than 2 minutes, and this process may be repeated at least 5 times, resulting in the ethanol processed skin, which may be stored, fully submerged in deionized water, at a temperature of from about 2° C. to about 8° C.

After ethanol treatment, the skin pieces may become white without any connective fat attached and some hair follicles on the skin surface may be exposed. Both the sodium hydroxide soaking and octanediol treatment steps may help disinfect the skin tissue by deactivating the function of possible bacteria and virus.

After the completion of the ethanol treatment, liquid collagen may be produced from the ethanol treated skin. First, a dissolving solution, such as a 0.01 to 0.5 M HCl dissolving solution may be prepared. 1 L of 0.01 to 0.5 M may be used per 10-20 g skin. Alternatively, acetic acid or any other suitable acid may be used as a dissolving solution. For example, the dissolving solution may comprise 0.2-2M acetic acid or 0.01-0.5M HCl. The dissolving solution and skin may be added to the tank. The air line may be turned on, and the speed of the mixer may be set such that the skin is stirred vigorously. The temperature may be set to about 4° C., and the skin may be allowed to soak for about 3 to about 72 hours. During soaking, the temperature may be monitored. If the temperature exceeds 8° C., degradation of collagen may occur, and the collagen solution should be discarded. The volume of the contents of the tank may be diluted five-fold by adding deionized water. This step may break down collagen matrix structure in porcine skin tissue and may solubilize collagen molecules in an acidic condition. At the end of the liquid collagen treatment steps, the liquid collagen may appear slightly opaque with small white chunks.

After the liquid collagen has been produced, it may undergo a collagen clarification process. The pH may be less than about 5. Next, the filtration equipment may be assembled by assembling the tubing, peristaltic pump, pressure gauge, and filter with the correct connections. The pressure regulator may be connected inline between the pump and a filter. The filters may be made of any suitable material and, in some embodiments, comprise polypropylene, glass fiber, polyethersulfone, or PTFE. The collagen solution may travel from the end of the tubing that lies in the sample vessel, into the pump, followed by the pressure regulator, and then into the filter. The solution exits the filter via the end of the tubing that has been placed into the collection vessel. Once the filtration equipment is assembled, multiple filtration steps may be performed on the skin, and the initial flow through may be discarded. For example, a first filtration step may use filters having a size of from about 20 to about 40 µm, a second filtration step may use filters having a size of from about 5 to about 10 µm, a third filtration step may use filters having a size of from about 0.8 to about 8 µm, and a fourth filtration step may use filters having a size of from about 0.22 to about 0.45 µm. The collagen solution is passed through each filter separately and sequentially from the largest pore size to the smallest. The solution may be purified until the pressure reaches about 40 psi, which may indicate that the filter has reached its capacity, and the tubing may rupture at the connection point with the filter. At this point, the fluid flow may either be decreased by half or the filter may be replaced with another of the same pore size. After each clarification step, about 5 mL of the liquid collagen may be collected for electrophoresis (SDS-PAGE) analysis. During clarification, the volume, pressure, and time at multiple points may be recorded. After clarification, the line may be washed with about 2 L of deionized water, and the clarified liquid collagen solution may be stored at a temperature of about 2° C. to about 8° C.

After clarification, the clarified liquid collagen solution may be concentrated. Concentration may be performed using a filtration system, such as a tangential flow filtration system. A specific example of a suitable system includes an AKTA flux machine. The filter media may comprise polysulfone and may have a pore size of from about 5,000 to about 100,000 molecular weight. However, the use of other similar systems is envisioned. Prior to concentration, the filtration system may be pre-cleaned.

After pre-cleaning is complete, concentration of the clarified liquid collagen may begin. To start the concentration process, certain settings on the AKTA flux machine may be set. Particularly, the following alarms may be activated: the upper limits of Pf, Pr, $\Delta P$, and TMP may be set to 3.7 barr. The upper and lower limits of the tank level may be set to 8 and 0.5 kg, respectively. A transfer tubing may be placed into the sample container. The transfer pump may be activated, such as to about 200 rpm, to transfer the liquid collagen from the storage container into the AKTA flux tank, and the mixer may be activated to about 80 rpm. Once the tank level reaches 4 kg, the feed pump may be set to run at about 800 rpm. The tank level auto control may be activated and set to 6.4 kg. The back pressure valve may be set to about halfway, and the permeate tube may be placed in the sink. Permeate may be periodically collected for later analysis.

Once the sample container is empty or the Pf is close to 3.6 barr, the Pf auto control may be set to 3.6 barr, causing the AKTA flux to vary the feed pump speed to maintain the pressure. The back pressure valve may be slowly released, ensuring the feed pump speed does not exceed 900 rpm. If this speed is exceeded, there may be a risk of the lines rupturing. A volume of the liquid collagen, such as about 5 mL, may be collected for SDS-PAGE analysis. When the pump speed has decreased to 100 rpm, the Pf auto control may be deactivated and the feed pump may be set to 100 rpm. The lower drain valve may be opened, and the concentrated collagen may be collected in a container, such as a sterile container, which may be sealed and stored at a temperature of from about 2° C. to about 8° C.

The concentration step may take from about 3 hours to about 48 hours, depending on the sample size and the filter size. The collagen solution may have a final concentration of from about 0.01 mg/mL to about 20 mg/mL, depending on the desired application.

Example 1: Extraction of Collagen from Porcine Skin

Fat and connective tissue were removed from porcine skin tissue by mechanical means (i.e., using a knife, scalpel, or skin peeling machine). The processed porcine skin tissue was washed with DI water, dried with paper towels, and weighed using a balance. The skin tissue was cut into small pieces (no larger than 5 cm by 0.5 cm) for further processing.

The porcine skin tissue was soaked in sodium hydroxide with a concentration between 0.2M and 1M and a temperature around 4° C. The ratio of skin tissue and sodium hydroxide solution was from 1 g:10 mL to 1 g:40 mL (skin weight to volume of sodium hydroxide solution). The sodium hydroxide soaking was conducted for 2 to 7 days with changing sodium hydroxide solution every day.

The resulting skin tissue was washed in DI water with about 1 g:30 mL skin to DI water ratio. The water bath was changed 3 times per day for 2 days. The solution was stirred in a refrigerator at around 4° C. for the duration of this step. The pH was reduced to about 8 after the washing.

After washing, the porcine skin tissue was soaked in 40% to 80% ethanol solution containing 5% to 10% octanediol. The solution was stirred at 37° C. for 1 to 3 days. The tissue was then washed with DI water several times to remove residual ethanol and octanediol.

The porcine skin tissue was dissolved in 0.2 to 2M acetic acid or 0.01 to 0.5M HCl with a 1 g:50 mL skin to acid ratio. This step was conducted at a temperature of about 4° C. for 3 to 48 hours until all skin tissue pieces were dissolved.

Figure 4:
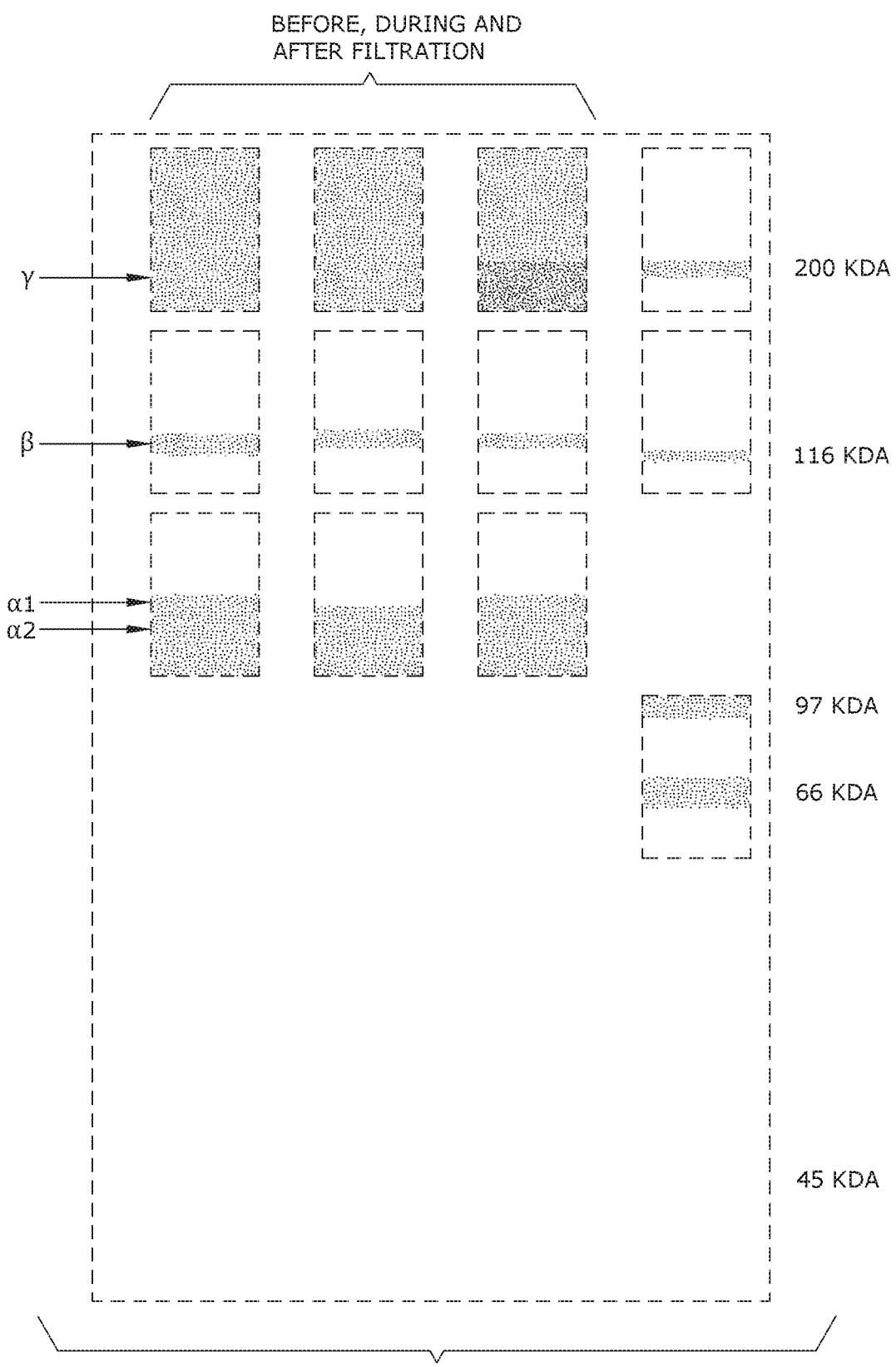
FIG. 4 is a graph of a SDS-PAGE of extracted and purified collagen, showing $\alpha$, $\beta$, and $\gamma$ bands of collagen and no band of any other protein, thus indicating other proteins from the skin tissue were removed during the treatment process of the present disclosure.

An SDS-PAGE experiment was used to detect whether there were any other proteins existing in the mixture after the process. As indicated by FIG. 4, following the process of the present disclosure resulted in extracted and purified collagen being collected, wherein no bands of any other protein were present, indicating that the treatment process of the present disclosure removed all other proteins from the skin tissue other than collagen.

Example 2: Purification of Collagen Solution Using a Multistage Filtration

The extracted collagen solution from Example 1 was first clarified using a strainer to remove residual large fats and particles. Then, the collagen solution was filtered using a series of four filters with different pore sizes, including 40 µm, 8 µm, 1.5 µm, and 0.22 µm capsule filters. The media material of these filters was polypropylene fibers. The collagen was diluted from 1 g: 50 mL to 1 g:500 mL using DI water for the steps of 8 µm, 1.5 µm, and 0.22 µm filtration. The maximum pressure of the filtration system was controlled to be lower than 40 PSI. The cloudiness of the dissolved collagen solution decreased significantly after every step of filtration.

After clarification filtration, a tangential flow filtration was used to concentrate the collagen solution. The TFF filter was a hollow fiber cartridge and had a pore size of 100,000 molecular weight. The filter fibers were made of polysulfone and had a diameter of about 1 mm. The collagen solution could be concentrated to 0.1 mg/mL to 20 mg/mL, depending on requirements in further applications or testing.

A hydroxyproline assay was used to measure the concentration of collagen in the resulting solution after all filtration and concentration steps. It was calculated that the overall yield of collagen from porcine skin tissue raw material was about 18.7%.

Figure 5:
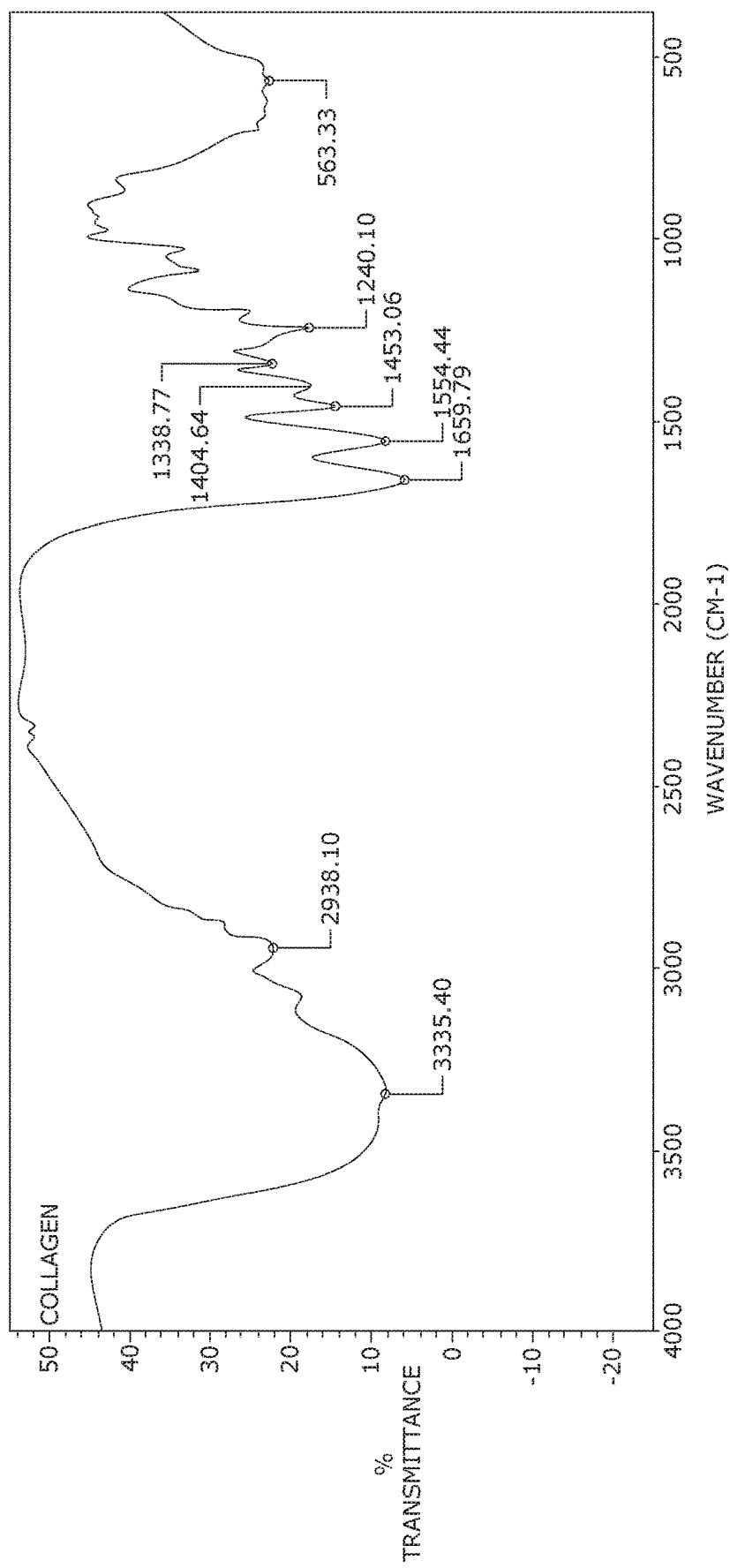
FIG. 5 is a FTIR spectra of processed liquid collagen showing experimental results for a particular example of one embodiment of the present disclosure.

FTIR spectroscopy was used to investigate chemical groups in the prepared collagen. FIG. 5 shows the FTIR spectra of processed liquid. In the spectra, amide I, II, and III bands at 1600 $cm^{-1}$, 1554 $cm^{-1}$, and 1240 $cm^{-1}$, respectively, are associated with typical spectrum patterns of collagen. The amide I is associated with the stretching vibrations of the carbonyl group along the polypeptide backbone. The amide II is associated with N—H bending vibrations, and the amide III is associated with C—H stretching.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A method of preparing a purified collagen solution from porcine skin, the method comprising:
   treating the porcine skin with a sodium hydroxide treatment, resulting in a sodium hydroxide processed skin;
   treating the sodium hydroxide processed skin with an ethanol treatment, resulting in ethanol treated processed skin, wherein treating the sodium hydroxide processes skin with the ethanol treatment comprises:
   preparing a first ethanol soaking solution in a tank;
   soaking the sodium hydroxide processed skin in the first ethanol soaking solution;
   removing the sodium hydroxide processed skin from the first ethanol soaking solution and washing the sodium hydroxide processed skin;
   soaking the sodium hydroxide processed skin in a second ethanol soaking solution; and
   removing the sodium hydroxide processed skin from the second ethanol soaking solution;
   producing liquid collagen from the ethanol treated processed skin;
   clarifying the liquid collagen; and
   concentrating the clarified liquid collagen,
   wherein:
   the first ethanol soaking solution comprises ethanol and 1,2-octanediol; and
   the second ethanol soaking solution comprises ethanol without 1,2-octanediol.

2. The method of claim 1, wherein treating the porcine skin with the sodium hydroxide treatment comprises:
   preparing a soaking solution of NaOH in a tank;
   soaking the porcine skin in the NaOH solution; and
   removing the skin from the soaking solution.

3. The method of claim 2, wherein:
   the porcine skin is soaked in the NaOH solution at a temperature of about 4° C. for about 10 to 20 hours; and
   the soaking is repeated a plurality of times.

4. The method of claim 2, wherein the soaking solution of NaOH comprises about 20 to about 30 mL of 1M NaOH for each gram of the porcine skin.

5. The method of claim 1, wherein:
   the sodium hydroxide processed skin is soaked in the first ethanol soaking solution for about 10 to about 20 hours; and
   the sodium hydroxide processed skin is soaked in the second ethanol soaking solution for about 4 to about 10 hours.

6. The method of claim 1, wherein producing liquid collagen from the ethanol processed skin comprises:
   preparing a HCl dissolving solution;
   adding the dissolving solution and the ethanol processed skin to a tank; and
   chilling the tank to a temperature of about 4° C.

7. The method of claim 6, wherein:
   the dissolving solution comprises about 1 L of 0.01M HCl for every 20 g of the ethanol processed skin; and
   the ethanol processed skin is soaked in the dissolving solution for about 72 hours.

8. The method of claim 1, wherein clarifying the liquid collagen comprises filtering the liquid collagen through multiple filtration steps.

9. The method of claim 8, wherein:
   a first filtration step uses filters having a size of from about 20 to about 40 µm;

a second filtration step uses filters having a size of from about 5 to about 10 μm;
a third filtration step uses filters having a size of from about 0.8 to about 8 μm; and
a fourth filtration step uses filters having a size of from about 0.22 to about 0.45 μm.

10. The method of claim 1, wherein concentrating the clarified liquid collagen comprises using a tangential flow filtration system.

\* \* \* \* \*